(12) United States Patent
Loudin et al.

(10) Patent No.: US 9,764,150 B2
(45) Date of Patent: Sep. 19, 2017

(54) CONTACT LENS FOR INCREASING TEAR PRODUCTION

(71) Applicant: Oculeve, Inc., South San Francisco, CA (US)

(72) Inventors: James Donald Loudin, Houston, TX (US); Manfred Franke, Redwood City, CA (US); Daniel N. Hamilton, Napa, CA (US); Anand Doraiswamy, San Francisco, CA (US); Douglas Michael Ackermann, San Francisco, CA (US)

(73) Assignee: Oculeve, Inc., South San Francisco, CA (US)

( * ) Notice: Subject to any disclaimer, the term of this patent is extended or adjusted under 35 U.S.C. 154(b) by 0 days.

(21) Appl. No.: 14/920,847

(22) Filed: Oct. 22, 2015

(65) Prior Publication Data

US 2016/0114172 A1 Apr. 28, 2016

Related U.S. Application Data

(60) Provisional application No. 62/067,395, filed on Oct. 22, 2014.

(51) Int. Cl.
*A61N 1/36* (2006.01)
*A61N 1/378* (2006.01)

(52) U.S. Cl.
CPC ....... *A61N 1/3787* (2013.01); *A61N 1/36046* (2013.01); *A61N 1/36121* (2013.01)

(58) Field of Classification Search
CPC .............. A61N 1/0526; A61N 1/36046; A61N 1/3606; A61N 1/375; A61N 1/3756; A61N 1/3787
See application file for complete search history.

(56) References Cited

U.S. PATENT DOCUMENTS 2,525,381 A * 10/1950 Tower ................... A61F 9/0017
351/159.02
4,520,825 A 6/1985 Thompson et al.
(Continued)

FOREIGN PATENT DOCUMENTS

EP 1497483 1/2005
EP 1651307 5/2006
(Continued)

OTHER PUBLICATIONS

Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
(Continued)

*Primary Examiner* — Eugene T Wu
(74) *Attorney, Agent, or Firm* — Cooley LLP

(57) ABSTRACT

Described here are devices, systems, and methods for increasing tear production by stimulating the cornea, conjunctiva, and/or subconjunctiva. In some variations, the devices may be in the form of a contact lens. The contact lens may comprise a lens body and a stimulator chip, where the stimulator chip is embedded in the lens body. An external power source wirelessly transmits energy to the stimulator chip, where the stimulator chip may convert the energy to an electric waveform to stimulate the cornea, conjunctiva, and/or subconjunctiva. Stimulation may activate the lacrimal reflex to increase tear production. The devices and systems for increasing tear production may be used in methods of treating dry eye, reducing the symptoms of tired eye, increasing comfort for contact lens wearers, and extending the number of years a contact lens user can wear contacts. Also described are methods of manufacturing a contact lens.

21 Claims, 8 Drawing Sheets

(56) References Cited

U.S. PATENT DOCUMENTS

| | | | |
|---|---|---|---|
| 4,539,988 A | 9/1985 | Shirley et al. | |
| 4,628,933 A | 12/1986 | Michelson | |
| 4,868,154 A | 9/1989 | Gilbard et al. | |
| 5,025,807 A | 6/1991 | Zabara | |
| 5,090,422 A | 2/1992 | Dahl et al. | |
| 5,099,829 A | 3/1992 | Wu | |
| 5,147,284 A | 9/1992 | Fedorov et al. | |
| 5,324,316 A | 6/1994 | Schulman et al. | |
| 5,345,948 A | 9/1994 | O'Donnell, Jr. | |
| 5,360,438 A | 11/1994 | Fisher | |
| 5,545,617 A | 8/1996 | Dartt et al. | |
| 5,607,461 A | 3/1997 | Lathrop | |
| 5,611,970 A * | 3/1997 | Apollonio | B29C 33/303 264/2.5 |
| 5,707,400 A | 1/1998 | Terry et al. | |
| 5,843,140 A | 12/1998 | Strojnik | |
| 5,948,006 A | 9/1999 | Mann | |
| 6,001,088 A | 12/1999 | Roberts et al. | |
| 6,035,236 A | 3/2000 | Jarding et al. | |
| 6,050,999 A | 4/2000 | Paraschac et al. | |
| 6,051,017 A | 4/2000 | Loeb et al. | |
| 6,083,251 A | 7/2000 | Shindo | |
| 6,152,916 A | 11/2000 | Bige | |
| 6,205,359 B1 | 3/2001 | Boveja | |
| 6,208,902 B1 | 3/2001 | Boveja | |
| 6,240,316 B1 | 5/2001 | Richmond et al. | |
| 6,246,911 B1 | 6/2001 | Seligman | |
| 6,272,382 B1 | 8/2001 | Faltys et al. | |
| 6,275,737 B1 | 8/2001 | Mann | |
| 6,277,855 B1 | 8/2001 | Yerxa | |
| 6,324,429 B1 | 11/2001 | Shire et al. | |
| 6,327,504 B1 | 12/2001 | Dolgin et al. | |
| 6,366,814 B1 | 4/2002 | Boveja et al. | |
| 6,458,157 B1 | 10/2002 | Suaning | |
| 6,505,077 B1 | 1/2003 | Kast et al. | |
| 6,535,766 B1 | 3/2003 | Thompson et al. | |
| 6,539,253 B2 | 3/2003 | Thompson et al. | |
| 6,564,102 B1 | 5/2003 | Boveja | |
| 6,658,301 B2 | 12/2003 | Loeb et al. | |
| 6,662,052 B1 | 12/2003 | Sarwal et al. | |
| 6,701,189 B2 | 3/2004 | Fang et al. | |
| 6,792,314 B2 | 9/2004 | Byers et al. | |
| 6,829,508 B2 | 12/2004 | Schulman et al. | |
| 6,871,099 B1 | 3/2005 | Whitehurst et al. | |
| 6,879,859 B1 | 4/2005 | Boveja | |
| 6,885,888 B2 | 4/2005 | Rezai | |
| 6,895,279 B2 | 5/2005 | Loeb et al. | |
| 7,024,241 B1 | 4/2006 | Bornzin et al. | |
| 7,054,692 B1 | 5/2006 | Whitehurst et al. | |
| 7,067,307 B2 | 6/2006 | Hochleitner et al. | |
| 7,069,084 B2 | 6/2006 | Yee | |
| 7,142,909 B2 | 11/2006 | Greenberg et al. | |
| 7,146,209 B2 | 12/2006 | Gross et al. | |
| 7,169,163 B2 | 1/2007 | Becker | |
| 7,190,998 B2 | 3/2007 | Shalev et al. | |
| 7,225,032 B2 | 5/2007 | Schmeling et al. | |
| 7,228,184 B2 | 6/2007 | Heath | |
| 7,317,947 B2 | 1/2008 | Wahlstrand et al. | |
| 7,330,762 B2 | 2/2008 | Boveja et al. | |
| 7,346,389 B1 * | 3/2008 | Newsome | A61F 9/0008 351/219 |
| 7,346,398 B2 | 3/2008 | Gross et al. | |
| 7,369,897 B2 | 5/2008 | Boveja et al. | |
| 7,442,191 B2 | 10/2008 | Hovda et al. | |
| 7,460,911 B2 | 12/2008 | Cosendai et al. | |
| 7,477,947 B2 | 1/2009 | Pines et al. | |
| 7,502,652 B2 | 3/2009 | Gaunt et al. | |
| 7,547,447 B2 | 6/2009 | Yiu et al. | |
| 7,565,204 B2 | 7/2009 | Matei et al. | |
| 7,599,737 B2 | 10/2009 | Yomtov et al. | |
| 7,636,597 B2 | 12/2009 | Gross et al. | |
| 7,650,186 B2 | 1/2010 | Hastings et al. | |
| D613,408 S | 4/2010 | Gausmann et al. | |
| D614,303 S | 4/2010 | Gausmann et al. | |
| D614,774 S | 4/2010 | Gausmann et al. | |
| 7,725,176 B2 | 5/2010 | Schuler et al. | |
| 7,725,195 B2 | 5/2010 | Lima et al. | |
| D617,443 S | 6/2010 | Grenon et al. | |
| 7,758,190 B2 | 7/2010 | Korb et al. | |
| 7,778,703 B2 | 8/2010 | Gross et al. | |
| 7,778,711 B2 | 8/2010 | Ben-David et al. | |
| 7,792,591 B2 | 9/2010 | Rooney et al. | |
| 7,805,200 B2 | 9/2010 | Kast et al. | |
| 7,805,202 B2 | 9/2010 | Kuzma et al. | |
| 7,805,203 B2 | 9/2010 | Ben-David et al. | |
| 7,809,442 B2 | 10/2010 | Bolea et al. | |
| 7,835,794 B2 | 11/2010 | Greenberg et al. | |
| 7,846,124 B2 | 12/2010 | Becker | |
| 7,860,570 B2 | 12/2010 | Whitehurst et al. | |
| 7,873,421 B2 | 1/2011 | Karell | |
| 7,879,079 B2 | 2/2011 | Tu et al. | |
| D638,128 S | 5/2011 | Prokop et al. | |
| 7,981,095 B2 | 7/2011 | Grenon et al. | |
| 7,998,202 B2 | 8/2011 | Lesh | |
| 8,019,419 B1 | 9/2011 | Panescu et al. | |
| 8,019,441 B2 | 9/2011 | Wallace et al. | |
| 8,145,322 B1 | 3/2012 | Yao et al. | |
| 8,165,680 B2 | 4/2012 | Greenberg et al. | |
| 8,204,591 B2 | 6/2012 | Ben-David et al. | |
| 8,318,070 B2 | 11/2012 | Shiah et al. | |
| 8,489,189 B2 | 7/2013 | Tronnes | |
| 8,494,641 B2 | 7/2013 | Boling et al. | |
| 8,918,181 B2 | 12/2014 | Ackermann et al. | |
| 8,996,137 B2 | 3/2015 | Ackermann et al. | |
| 9,079,042 B2 | 7/2015 | Tiedtke et al. | |
| 9,095,723 B2 | 8/2015 | Ackermann et al. | |
| 9,265,956 B2 | 2/2016 | Ackermann et al. | |
| 2001/0020177 A1 | 9/2001 | Gruzdowich et al. | |
| 2002/0013594 A1 | 1/2002 | Dinger et al. | |
| 2002/0035358 A1 | 3/2002 | Wang | |
| 2002/0188331 A1 | 12/2002 | Fang et al. | |
| 2003/0045909 A1 | 3/2003 | Gross et al. | |
| 2003/0114899 A1 | 6/2003 | Woods et al. | |
| 2003/0120323 A1 | 6/2003 | Meadows et al. | |
| 2003/0130809 A1 | 7/2003 | Cohen et al. | |
| 2003/0139784 A1 * | 7/2003 | Morimoto | A61N 1/36046 607/54 |
| 2003/0192784 A1 | 10/2003 | Zhou et al. | |
| 2003/0233134 A1 | 12/2003 | Greenberg et al. | |
| 2004/0050392 A1 | 3/2004 | Tu et al. | |
| 2004/0059466 A1 | 3/2004 | Block et al. | |
| 2004/0098067 A1 | 5/2004 | Ohta et al. | |
| 2004/0147973 A1 | 7/2004 | Hauser et al. | |
| 2005/0004621 A1 | 1/2005 | Boveja et al. | |
| 2005/0010250 A1 | 1/2005 | Schuler et al. | |
| 2005/0010266 A1 * | 1/2005 | Bogdanowicz | A61N 1/32 607/53 |
| 2005/0101967 A1 | 5/2005 | Weber et al. | |
| 2005/0105046 A1 | 5/2005 | Tung | |
| 2005/0197675 A1 | 9/2005 | David et al. | |
| 2005/0251061 A1 | 11/2005 | Schuler et al. | |
| 2005/0267542 A1 | 12/2005 | David et al. | |
| 2006/0004423 A1 | 1/2006 | Boveja et al. | |
| 2006/0074450 A1 | 4/2006 | Boveja et al. | |
| 2006/0095077 A1 | 5/2006 | Tronnes et al. | |
| 2006/0095108 A1 | 5/2006 | Chowdhury et al. | |
| 2006/0100668 A1 | 5/2006 | Ben-David et al. | |
| 2006/0142822 A1 | 6/2006 | Tulgar | |
| 2006/0161225 A1 | 7/2006 | Sormann et al. | |
| 2006/0195169 A1 | 8/2006 | Gross et al. | |
| 2006/0206155 A1 | 9/2006 | Ben-David et al. | |
| 2006/0235430 A1 | 10/2006 | Le et al. | |
| 2006/0239482 A1 | 10/2006 | Hatoum et al. | |
| 2006/0259098 A1 | 11/2006 | Erickson | |
| 2006/0271108 A1 | 11/2006 | Libbus et al. | |
| 2007/0038267 A1 | 2/2007 | Shodo et al. | |
| 2007/0060815 A1 | 3/2007 | Martin et al. | |
| 2007/0060954 A1 | 3/2007 | Cameron et al. | |
| 2007/0150034 A1 | 6/2007 | Rooney et al. | |
| 2007/0250119 A1 | 10/2007 | Tyler et al. | |
| 2007/0250135 A1 | 10/2007 | Bartz-Schmidt et al. | |
| 2007/0276314 A1 | 11/2007 | Becker | |
| 2008/0021515 A1 | 1/2008 | Horsager et al. | |
| 2008/0082131 A1 | 4/2008 | Llanos | |

(56) References Cited

U.S. PATENT DOCUMENTS

| | | |
|---|---|---|
| 2008/0109054 A1 | 5/2008 | Hastings et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208335 A1* | 8/2008 | Blum .................. A61F 2/1616 623/6.22 |
| 2008/0294066 A1* | 11/2008 | Hetling ................ A61B 5/0496 600/558 |
| 2009/0005835 A1 | 1/2009 | Greenberg et al. |
| 2009/0024187 A1 | 1/2009 | Erickson et al. |
| 2009/0024189 A1 | 1/2009 | Lee et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0204142 A1 | 8/2009 | Becker |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0306738 A1 | 12/2009 | Weiss et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0274313 A1 | 10/2010 | Boling et al. |
| 2010/0280509 A1 | 11/2010 | Muller et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0082518 A1* | 4/2011 | Filippello ............ A61N 1/0452 607/53 |
| 2011/0093043 A1 | 4/2011 | Torgerson et al. |
| 2011/0152969 A1 | 6/2011 | Zehnder et al. |
| 2011/0202121 A1 | 8/2011 | Wen |
| 2011/0276107 A1 | 11/2011 | Simon et al. |
| 2011/0295336 A1 | 12/2011 | Sharma et al. |
| 2012/0130398 A1* | 5/2012 | Ackermann ....... A61N 1/36046 606/129 |
| 2012/0197338 A1 | 8/2012 | Su et al. |
| 2012/0232615 A1 | 9/2012 | Barolat et al. |
| 2012/0253249 A1 | 10/2012 | Wilson et al. |
| 2012/0323227 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1* | 1/2013 | Ackermann ....... A61N 1/36046 607/53 |
| 2013/0178937 A1 | 7/2013 | Vassallo et al. |
| 2013/0261706 A1 | 10/2013 | Mirro et al. |
| 2013/0304154 A1 | 11/2013 | Goodman et al. |
| 2014/0163580 A1 | 6/2014 | Tischendorf et al. |
| 2014/0214120 A1 | 7/2014 | Simon et al. |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316485 A1 | 10/2014 | Ackermann et al. |
| 2014/0371565 A1* | 12/2014 | Glasser .............. A61N 1/36046 600/383 |
| 2014/0371812 A1 | 12/2014 | Ackermann et al. |
| 2015/0088156 A1 | 3/2015 | Ackermann et al. |
| 2015/0335900 A1 | 11/2015 | Ackermann et al. |
| 2015/0362755 A1* | 12/2015 | Lee ..................... G02C 7/04 351/159.4 |
| 2016/0022992 A1 | 1/2016 | Franke et al. |
| 2016/0114163 A1 | 4/2016 | Franke et al. |
| 2016/0121118 A1 | 5/2016 | Franke et al. |

FOREIGN PATENT DOCUMENTS

| | | |
|---|---|---|
| EP | 1919553 | 5/2008 |
| EP | 1958661 A1 | 8/2008 |
| EP | 2205193 | 7/2010 |
| EP | 2205314 | 7/2010 |
| JP | 2002-325851 A | 11/2002 |
| JP | 2002-539859 A | 11/2002 |
| JP | 2005-052461 A | 3/2005 |
| JP | 2006-515900 A | 6/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2010-505563 A | 2/2010 |
| JP | 2010-051562 A | 3/2010 |
| JP | 2010-537777 A | 12/2010 |
| JP | 2011-030734 A | 2/2011 |
| WO | WO-00/56393 A1 | 9/2000 |
| WO | WO-00/62672 A1 | 10/2000 |
| WO | WO-03/087433 A1 | 10/2003 |
| WO | WO-2004/026106 A2 | 4/2004 |
| WO | WO-2004/026106 A3 | 4/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/060984 A1 | 7/2005 |
| WO | WO-2006/127366 A1 | 11/2006 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/070709 A1 | 6/2009 |
| WO | WO-2010/003011 A1 | 1/2010 |
| WO | WO-2010/027743 A1 | 3/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2014/138709 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/065211 A1 | 4/2016 |
| WO | WO-2016/065213 A1 | 4/2016 |
| WO | WO-2016/065215 A1 | 4/2016 |

OTHER PUBLICATIONS

Calonge (2001). "The Treatment of Dry Eye," Survey Ophth. 45(2)S227-S239.

Elsby et al. (1967). "Lacrimal Secretion in the Cat," Br. J. Pharm. Chemother. 29(1):1-7.

Extended European Search Report received for European Patent Application No. 11842076.9, mailed on Oct. 10, 2014, 5 pages.

Extended European Search Report received for European Patent Application No. 12768458.7, mailed on Aug. 28, 2014, 7 pages.

Extended European Search Report mailed on Oct. 21, 2016, for EP Application No. 14 778 719.6, filed on Mar. 12, 2014, 8 pages.

Final Office Action received for U.S. Appl. No. 13/441,806, mailed on Mar. 12, 2015.

Final Office Action received for U.S. Appl. No. 13/441,806, mailed on May 20, 2016.

Final Office Action received for U.S. Appl. No. 14/816,846, mailed on May 11, 2016, 12 pages.

Final Office Action received for U.S. Appl. No. 14/207,072, mailed on Jun. 22, 2016.

(56) References Cited

OTHER PUBLICATIONS

Final Office Action mailed on Sep. 23, 2016, for U.S. Appl. No. 14/809,109, filed Jul. 24, 2015, 10 pages.
International Search Report & Written Opinion received for PCT Patent Application No. PCT/US2011/060989, mailed on Feb. 23, 2012.
International Search Report & Written Opinion received for PCT Patent Application No. PCT/US2014/022158, mailed on Jul. 30, 2014.
International Search Report and Written Opinion received for PCT Application No. PCT/US2015/042130, mailed on Oct. 28, 2015.
International Search Report and Written Opinion received for PCT Patent Application No. PCT/US2015/057023, mailed on Mar. 4, 2016.
International Search Report and Written Opinion received for PCT Patent Application No. PCT/US2014/024496, mailed on Aug. 22, 2014, 11 pages.
International Search Report received for PCT Patent Application No. PCT/US2012/32629, mailed on Oct. 26, 2012.
International Search Report received for PCT Patent Application No. PCT/US2015/57021, mailed on Feb. 10, 2016.
International Search Report received for PCT Patent Application No. PCT/US2015/57019, mailed on Feb. 11, 2016, 4 pages.
Lora et al. (2009). "Lacrimal Nerve Stimulation by a Neurostimulator for Tear Production," Invest. Ophth. Vis. Science 50(13):172.
Meng, I.D. et al. (2013). "The role of corneal afferent neurons in regulating tears under normal and dry eye conditions," Exp. Eye Res. 117:79-87.
Non-Final Office Action received for U.S. Appl. No. 13/441,806, mailed on Sep. 17, 2015.
Non-Final Office Action received for U.S. Appl. No. 13/298,042, mailed on Oct. 2, 2013.
Non-Final Office Action received for U.S. Appl. No. 13/441,806, mailed on Dec. 18, 2013.
Non-Final Office Action received for U.S. Appl. No. 14/201,753, mailed on Apr. 2, 2015.
Non-Final Office Action received for U.S. Appl. No. 14/809,109, mailed on Apr. 8, 2016.
Non-Final Office Action for U.S. Appl. No. 14/816,846, mailed on Sep. 11, 2015.
Non-Final Office Action received for U.S. Appl. No. 14/920,860, mailed Aug. 17, 2016.
Non-Final Office Action Received for U.S. Appl. No. 14/920,852, mailed on Aug. 1, 2016.
Non-Final Office Action received for U.S. Appl. No. 14/207,072, mailed on Dec. 9, 2015.
Non-Final Office Action mailed on Nov. 2, 2016, for U.S. Appl. No. 13/441,806, filed Apr. 6, 2012, 11 pages.
Non-Final Office Action mailed on Dec. 6, 2016, for U.S. Appl. No. 14/816,846, filed Aug. 3, 2015, 13 pages.
Notice of Allowance received for U.S. Appl. No. 14/201,753, mailed on Dec. 15, 2015.
Notice of Allowance received for U.S. Appl. No. 14/201,753, mailed on Oct. 15, 2015.
Notice of Allowance received for U.S. Appl. No. 13/298,042, mailed on Apr. 29, 2014.
Notice of Allowance received for U.S. Appl. No. 13/298,042, mailed on Aug. 11, 2014.
Notice of Allowance received for U.S. Appl. No. 13/298,042, mailed on Nov. 13, 2014.
Notice of Allowance received for U.S. Appl. No. 14/561,107, mailed on Mar. 31, 2015.
Notice of Allowance mailed on Dec. 19, 2016, for U.S. Appl. No. 14/809,109, filed Jul. 24, 2015, 8 pages.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2012/032629, mailed on Oct. 26, 2012, 8 pages.
Written Opinion received for PCT Patent Application No. PCT/US2015/57021, mailed on Feb. 10, 2016.
Written Opinion received for PCT Patent Application No. PCT/US2015/57019, mailed on Feb. 11, 2016, 6 pages.

\* cited by examiner

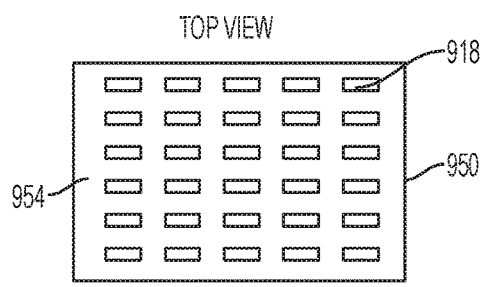
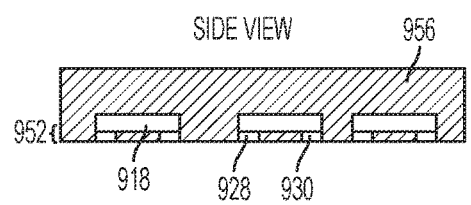
FIG. 9A    FIG. 9B
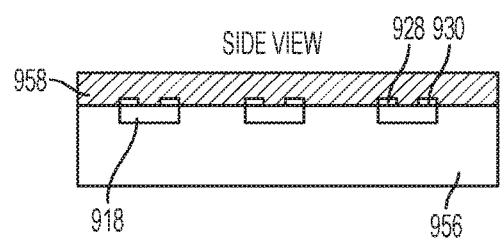
FIG. 9C
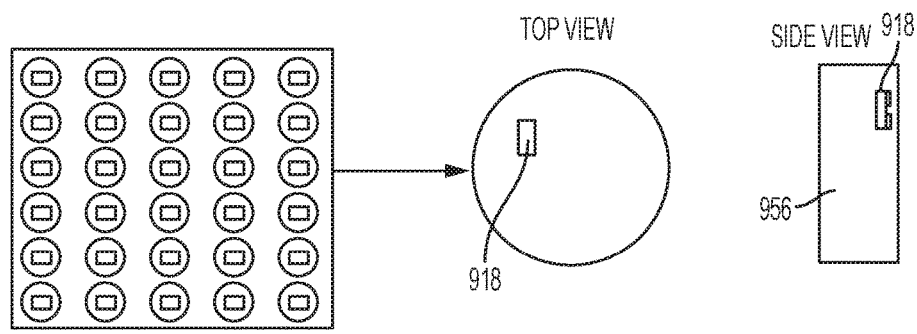
FIG. 9D

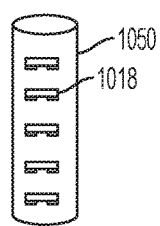 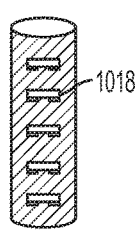 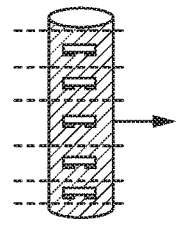 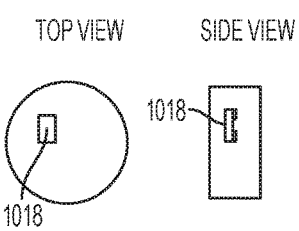
FIG. 10A   FIG. 10B   FIG. 10C   FIG. 10D
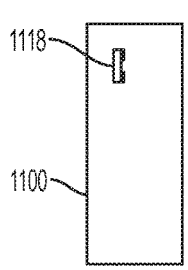 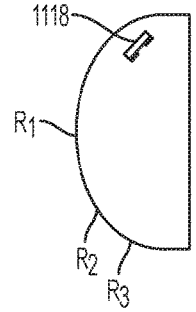 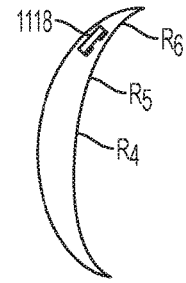
FIG. 11A   FIG. 11B   FIG. 11C

CONTACT LENS FOR INCREASING TEAR PRODUCTION

CROSS-REFERENCE TO RELATED APPLICATIONS

This application claims priority to U.S. Provisional Patent Application No. 62/067,395, filed on Oct. 22, 2014, and titled "CONTACT LENS FOR INCREASING TEAR PRODUCTION," which is hereby incorporated by reference in its entirety.

FIELD

The present disclosure relates generally to stimulation devices, systems, and methods of use thereof. The stimulation systems may be used to stimulate the cornea and/or conjunctiva and/or subconjunctiva of the eye to increase tear production in the treatment of one or more indications, such as dry eye.

BACKGROUND

Dry eye is a condition that affects millions of people. More than 40 million people in North America have some form of dry eye, and many millions more suffer worldwide. Dry eye results from the disruption of the natural tear film on the surface of the eye, and can result in ocular discomfort, visual disturbance and a reduction in vision-related quality of life. Activities of daily living such as driving, computer use, housework, and reading have also been shown to be negatively impacted by dry eye. Patients with severe cases of dry eye are at risk for serious ocular health deficiencies such as corneal ulceration, and can experience a quality of life deficiency comparable to that of moderate-severe angina.

Dry Eye Disease ("DED") is a clinical condition of the eye. DED is progressive in nature, and fundamentally results from insufficient tear coverage on the surface of the eye. This poor tear coverage prevents healthy gas exchange and nutrient transport for the ocular surface, promotes cellular desiccation, and creates a poor refractive surface for vision. Poor tear coverage typically results from: 1) insufficient aqueous tear production from the lacrimal glands (e.g. secondary to post-menopausal hormonal deficiency, autoimmune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells, which in turn prevents proper distribution of the tear film on the ocular surface so that any given tear volume is rendered less effective. This initiates a vicious cycle where more inflammation can ensue, causing more surface cell damage, etc.

External factors that are not clinically based may also contribute to dry eye. These factors can include medications, dehydration, and environmental pollutants. Contact lenses, particularly soft contact lenses, are also known to cause or exacerbate the symptoms of dry eye. The contact lenses continually absorb water from the surface of the tear film in order to keep hydrated, leading to dryness of the eye. Dry eye can also be a symptom of the condition commonly known as "tired eye." During extended periods of focused, intense use, such as heavy computer use and long distance driving, the eyes strain and blink less frequently, which can lead to insufficient lubrication of the eyes (i.e., dry eye).

There is a wide spectrum of treatments for dry eye, although without substantial efficacy for treatment of the condition. Treatment options include: artificial tear substitutes, ointments, gels, warm compresses, environmental modification, topical cyclosporine, omega-3 fatty acid supplements, punctal plugs, and moisture chamber goggles. Patients with severe disease may further be treated with punctal cautery, systemic cholinergic agonists, systemic anti-inflammatory agents, mucolytic agents, autologous serum tears, PROSE scleral contact lenses, and tarsorrhaphy. Despite these treatment options, dry eye continues to be considered one of the most poorly treated diseases in ophthalmology. Accordingly, it would be desirable to have a more effective treatment for dry eye.

BRIEF SUMMARY

Described here are devices, systems, and methods for increasing tear production by stimulating the cornea, conjunctiva, and/or subconjunctiva. Generally, the devices and systems may be configured to electrically stimulate the cornea and/or conjunctiva and/or subconjunctiva. In some variations, the devices may comprise a stimulator chip. An external power source may wirelessly transmit energy to the stimulator chip, where the stimulator chip may convert the energy transmitted to an electric waveform and electrically stimulate the cornea, conjunctiva and/or subconjunctiva. Stimulation may activate reflex pathways to increase tear production. The devices and systems for increasing tear production may be used in methods of treating dry eye, reducing the symptoms of tired eye, increasing comfort for contact lens wearers, and extending the number of years a contact lens user can wear contacts. Also described are methods of manufacturing a contact lens, where the contact lens is configured to increase tear production by stimulating the cornea, conjunctiva, and/or subconjunctiva.

In some variations, the devices described here may comprise lens devices for increasing tear production by stimulating the cornea, conjunctiva, and/or subconjunctiva of a subject. The devices may be in the form of a contact lens for placement on the cornea/conjunctiva of the eye. The contact lens may comprise a lens body and a stimulator chip, where the stimulator chip is within the lens body. Energy transmitted from the external power source to the stimulator chip may be converted to electrically stimulate the cornea, conjunctiva, and/or subconjunctiva. The lacrimal pathway may be initiated with activating sensory components in the cornea, conjunctiva, subconjunctiva, or surrounding orbital tissue. Stimulation may activate the lacrimal reflex to increase tear production.

In some variations, the devices described here may comprise implantable devices for increasing tear production by stimulating the cornea, conjunctiva, and/or subconjunctiva of a subject. In some variations, the device may be in the form of an implantable device comprising a stimulator chip. The implantable device may utilize reflex pathways to activate the lacrimal gland, and in some cases the accessory glands, such as krause, zeiss, and meibomian glands, to increase tear production and tear quality. The implantable device may be placed subconjunctivally.

In some variations, the systems described here comprise systems for increasing tear production by stimulating the cornea, conjunctiva, and/or subconjunctiva of a subject. In some variations, the system may comprise a device having a stimulator chip and an external power source. The external power source may be handheld or mountable for mounting to locations adjacent to where a patient may look for extended periods of time (e.g., a computer monitor, car windshield, television, etc.). The stimulator chip may receive wireless energy from the external power source and provide an electric stimulation waveform to the corneal and/or conjunctival innervation of the eye to increase tear production. In some variations, the external power source may be a laser diode or a light-emitting diode (LED), which may in some instances emit infrared (IR) light.

In some variations, the methods described here may comprise methods for increasing tear production in a subject. In some variations, the methods for increasing tear production may be used for treating DED caused by clinical factors, such as dysfunction of the lacrimal and/or meibomian glands. The treatment may also be for dry eye caused by external factors, such as medications, dehydration, and environmental pollutants. In some variations, the methods for increasing tear production may be for increasing comfort for contact lens wearers. In some variations, the methods for increasing tear production may be for reducing the symptoms of tired eye in patients not diagnosed as having DED. In some variations, the methods for increasing tear production may be for extending the number of years a contact lens user can wear contacts. The methods may comprise the step of stimulating the cornea, conjunctiva, and/or subconjunctiva to activate the reflex pathway and increase lacrimation.

In some variations, the methods described here comprise methods of manufacturing a contact lens configured to increase tear production by stimulating the cornea, conjunctiva, and/or subconjunctiva. The method of manufacturing a contact lens may comprise the step of embedding a stimulator chip in a lens body by sheet casting or rod casting. The method may further comprise the step of lathe cutting the casting to a desired shape. In some variations, the method of manufacturing a contact lens may comprise embedding a stimulator chip in a lens body and shaping the lens body by direct cast molding.

In some variations, the devices described here comprise a contact lens for increasing tear production in an eye of a subject. In some variations, the contact lens comprises a lens body configured for placement on a surface of the eye, and a stimulator chip configured to stimulate a cornea or a conjunctiva of the eye, where the stimulator chip is embedded within the lens body. In some variations, the lens body is a corrective lens. In some of these variations, the corrective lens is toric, aspheric, multifocal, diffractive, or scleral. In some variations, the lens body is non-corrective or non-refractive and has a zero power. In some variations, the lens body has a posterior surface configured to contact the conjunctiva of the eye, and the stimulator chip is embedded in the lens body within 20 microns of the posterior surface. In some variations, the stimulator chip is embedded in a portion of the lens body that is configured to cover an iris of the eye when the lens body is placed on the surface of the eye. In some variations, the stimulator chip is embedded in a portion of the lens body that is configured to be in front of an iris of the eye when the lens body is placed on the cornea of the eye. In some variations, the contact lens comprises a counterweight located approximately 180 degrees from the stimulator chip. In some of these variations, the counterweight is a second stimulator chip. In some variations, the contact lens comprises one or more weights for minimizing rotation of the contact lens. In some of these variations, the one or more weights is a second stimulator chip. In some variations, the stimulator chip is configured to receive energy wirelessly from an external power source and to convert the energy to a stimulation signal for electrically stimulating the cornea or the conjunctiva. In some of these variations, the stimulator chip comprises a power receiver configured to receive the energy wirelessly and to convert the energy to an electric signal. In some of these variations, the stimulator chip further comprises a signal conditioning unit configured to receive the electric signal and to modify the electric signal into an electric output. In some of these variations, modifying the electric signal comprises modifying one or more of a frequency, a shape, and an amplitude of the electric signal. In some variations, the stimulator chip further comprises electrode contacts configured to deliver the electric output to the cornea or the conjunctiva. In some of these variations, the electric output has a frequency that varies over time. In others of these variations, the electric output has a pulse width that varies over time. In some variations, the stimulator chip comprises a photodiode. In some variations, the stimulator chip comprises an integrated circuit. In some variations, the stimulator chip has a thickness between approximately 5 microns and 100 microns. In some of these variations, the thickness of the stimulator chip is approximately 20 microns.

In some variations, the systems described here are for increasing tear production in an eye of a subject. In some variations, the systems comprise a device configured for placement on a cornea, or in a subconjunctiva of the eye, where the device comprises a stimulator chip configured to stimulate the cornea or a conjunctiva of the eye, and an external power source for transmitting energy wirelessly to the stimulator chip to activate the stimulator chip. In some variations, the external power source is handheld. In other variations, the external power source is mountable. In some variations, the external power source comprises a laser diode. In some of these variations, the laser diode produces light comprising wavelengths between approximately 880 nm and 930 nm. In some variations, the external power source comprises an infrared light-emitting diode. In other variations, the external power source comprises an optical modifier to produce non-collimated light. In some of these variations, the optical modifier comprises a condenser lens and a microlens array. In some variations, the stimulator chip comprises a photodiode.

Also described here are methods of increasing tear production in a subject. In some variations, the methods comprise transmitting energy wirelessly from an external power source to a stimulator chip, where the stimulator chip is located in a subconjunctval space of an eye of the subject or is embedded in a contact lens worn by the subject, and delivering a stimulus from the stimulator chip to a conjunctiva or a cornea of the eye to produce tears. In some variations, the stimulator chip comprises a photodiode, and the external power source comprises a light source. In some of these variations, the light source comprises a laser diode. In other of these variations, the light source comprises an infrared light-emitting diode. In some variations, the method further comprises moving the eye to expose the photodiode to the light source. In some variations, the external power source is fixed to a location selected from the group consisting of a computer monitor, a car windshield, a television, and a forward face of a smart phone or a tablet. In some variations, the stimulator chip is within an implantable device located in the subconjunctval space of the eye. In some of these variations, the implantable device is secured in the subconjunctval space of the eye by one or more anchors. In some variations, the method further comprises periodically replacing the implantable device. In some of these variations, replacing the implantable device comprises removing the existing implantable device from a first location and placing a new implantable device in a second location. In some variations, the subject has dry eye, and the method of increasing tear production is used to treat the dry eye. In some variations, the subject is at an increased risk of developing dry eye, and the method of increasing tear production is used for prophylactic treatment of dry eye. In some variations, the subject has ocular allergies, and method of increasing tear production is used to treat the ocular allergies. In some variations, the subject wears contact lenses, and the method of increasing tear production is used for increasing comfort of wearing contact lenses. In some variations, the subject wears contact lenses, and the method of increasing tear production is used for extending a time period for which the subject can comfortably wear contact lenses. In some variations, the subject wears contact lenses, and the method of increasing tear production is used for extending a number of years for which the subject can wear contact lenses. In some variations, the subject has tired eye, and the method of increasing tear production is used for reducing symptoms of tired eye.

Also described here are methods for manufacturing a contact lens configured to treat dry eye. In some variations, the method comprises embedding a stimulator chip in a lens body, and shaping the lens body. In some variations, embedding comprises sheet casting. In other variations, embedding comprises rod casting. In some variations, shaping comprises lathe cutting. In some variations, the method comprises cast molding. In some variations, the contact lens has a posterior surface configured to contact a conjunctiva of an eye, and the stimulator chip is embedded in the lens body proximate to the posterior surface at a distance sufficient to allow for effective stimulation of a cornea and/or the conjunctiva of the eye by the stimulator chip.

BRIEF DESCRIPTION OF THE DRAWINGS

FIGS. 9A-9D show an illustrative variation of a method of manufacturing a contact lens using sheet casting;

FIGS. 10A-10D show an illustrative variation of a method of manufacturing a contact lens using rod casting;

FIGS. 11A-11C show an illustrative variation of the shaping of a contact lens from button form to a meniscus lens using lathe cutting;

DETAILED DESCRIPTION

Described here are devices, systems, and methods for increasing tear production by stimulating the cornea, conjunctiva, and/or subconjunctiva. The device may be a contact lens or an implantable device, which may comprise a stimulator chip. The system may comprise the contact lens or implantable device and an external power source that may wirelessly transmit energy to the stimulator chip. The stimulator chip may convert the energy transmitted to an electric waveform, which may be delivered to a subject to electrically stimulate the cornea, conjunctiva, and/or subconjunctiva. This may in turn activate the reflex pathways and increase tear production.

The devices and systems for increasing tear production described here may be used in methods of treating dry eye caused by clinical and/or external factors. They may also be used in methods of reducing the symptoms of tired eye, increasing comfort for contact lens wearers, and extending the number of years a contact lens user can wear contacts. Also described are methods of manufacturing a contact lens, where the contact lens is configured to increase tear production by stimulating the cornea and/or conjunctiva.

Devices

The devices described here may be for placement on the cornea or for placement in the subconjunctiva of the eye. The devices may comprise a stimulator chip for electrically stimulating the cornea and/or conjunctiva to increase lacrimation in patients suffering from dry eye, tired eye, and other conditions.

Contact Lens

Figure 1:
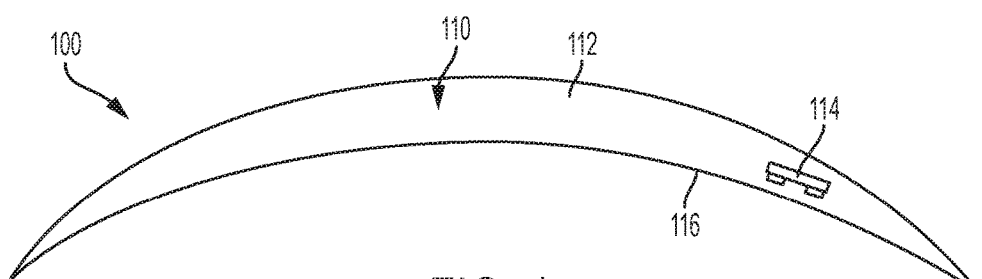
FIG. 1 shows a cut-away side view of an illustrative variation of a contact lens with a stimulator chip.

As shown in FIG. 1, device 100 is in the form a contact lens 110 for placement on the cornea/conjunctiva of the eye. The contact lens 110 has a lens body 112 made from a biomaterial. The biomaterial can be any optically clear and biologically compatible material. Classifications of acceptable biomaterials include, but are not limited to: hydrophilic acrylates, hydrophobic acrylates, rigid poly(methyl methacrylate) (PMMA), and polyurethanes. Also acceptable are hydrogel materials, including but not limited to: silicone hydrogels, silicone acrylates (SAs), fluoro-silicone acrylates, and various gas-permeable materials. The biomaterial may be ionic or non-ionic, and may have a high water content or low water content, such as ranging from about 30% to about 70%. In some variations, the contact lens may have a monoblock lens body. In other variations, the contact lens may have a hybrid lens body comprising a soft, pliable, optically clear center portion and a rigid perimeter portion made from a rigid gas permeable material.

The contact lens may be corrective having a power specific to the patient's needs. The contact lens may also be a toric, aspheric, multifocal, diffractive, scleral, or other type of corrective contact lens. Alternatively, the lens may be non-corrective/refractive (i.e., zero power) for patients who do not require corrective lenses but suffer from dry eye, tired eye, or other eye conditions. The lens also may be a bandage contact lens for protecting and healing the eye and increasing comfort for patients with damaged or compromised corneas.

Contact lens 110 comprises a stimulator chip 114 within the lens body 112. Stimulator chip 114 may be configured to convert wireless energy transmitted from an outside source to an electric waveform for electrically stimulating the cornea/conjunctiva. Stimulator chip 114 is embedded in the lens body 112 and is positioned close to the posterior surface 116 adjacent to the eye. Close proximity of the stimulator chip to the eye surface may allow for effective stimulation of the cornea and/or conjunctiva. Accordingly, in some variations, the stimulator chip may be within 5 microns, within 10 microns, or within 10-20 microns of the posterior surface of the lens. Larger stimulators may be positioned further from the posterior surface. In other variations, the stimulator chip may be within 50-100 microns of the posterior surface. In other variations, such as with hybrid lens bodies described herein, the stimulator chip may be mounted directly to the surface of the lens body. The stimulator chip may be located in a number of positions in the lens body, but it may be desirable for the stimulator chip to be located in the portion of the lens body that covers the iris of the eye when inserted, so as to avoid blocking the visual axis.

Figure 2:
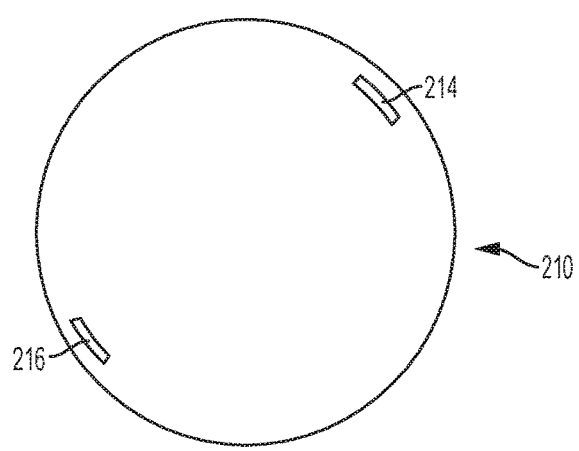
FIG. 2 shows a front view of an illustrative variation of a contact lens having a stimulator chip and a counterweight.

In some instances it may be desirable that the contact lens be rotationally unstable to allow repositioning of the stimulator chip when blinking. This may reduce accommodation and habituation to the stimulus. In one variation, a single stimulator chip embedded in the lens body is light enough in weight to not unbalance the contact lens or prevent repositioning. In another variation, shown in FIG. 2, a counterweight 216 is located approximately 180 degrees from a first stimulator chip 214 in order to balance the weight and prevent the first stimulator chip 214 from weighing down and inhibiting rotation of contact lens 210. The counterweight 216 may be, for example, another stimulator chip, but may also be an inactive chip or any suitable object having appropriate weight and size.

However, in other instances such rotational instability may be undesirable. For example, contact lenses used for astigmatism are generally toric lenses having different optical power and focal length in two perpendicular orientations. In these cases, rotation of the lens may negatively affect vision, and therefore may not be desirable. In some variations for addressing astigmatism, one, two, or more inactive chips, or other weights, may be placed in the lower portion of the lens body in order to help the lens find a specific orientation and minimize rotation.

Implantable Device

In another variation, the device may be in the form of an implantable device. The implantable device may comprise a stimulator chip that is implanted within the eye and may utilize reflex pathways to provide activation to the lacrimal gland to increase tear production, and in some cases to provide activation of the accessory glands.

Figure 3:
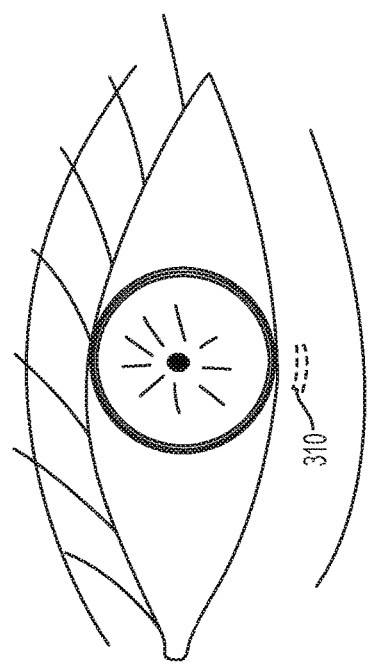
FIG. 3 shows an illustrative implantable device implanted in a position behind the lower eyelid.

The implantable device may in some instances be placed subconjunctivally. The implantable device may be implanted in any location in the subconjunctiva where the stimulator chip can be exposed to energy transmission from an external power source. As shown in FIG. 3, it may be preferable for an implantable device 310 to be implanted in the subconjunctiva behind an eyelid (e.g., the lower eyelid) to avoid cosmetic impact. In this location, the implantable device 310 may be hidden when the subject looks straight ahead or side-to-side, but may become exposed when looking up. In other variations, the implantable device may be implanted such that it is visible when the subject looks straight ahead or side-to-side. In these cases, the implant may be configured with a decorative shape and/or distinct color (e.g., a red heart), so as to appear to be eye jewelry.

Because the conjunctiva defines an open space between it and the cornea, an implantable device inserted in the subconjunctival space may tend to migrate. Accordingly, the implantable device may comprise one or more fixation features to secure it in place. In some variations, fixation features may include one or multiple feet extending from the device. The feet may measure approximately 50-100 microns in length. In some instances, the feet may be pushed into the sclera for anchorage. Fixation features may also include an angled pick or nail for holding the device in place, biocompatible glue for initial fixation, or any other suitable anchoring feature.

The stimulator chip may have a coating of a thickness that allows the stimulation device to be atraumatic and non-irritating when implanted in the eye, but close enough to the conjunctiva to stimulate the nerves therein. Close proximity of the stimulator chip to the eye surface may allow for effective stimulation of the cornea, conjunctiva, and/or subconjunctiva, while exposure may result in a foreign body sensation and irritation. Accordingly, in some variations, the stimulator chip may have a coating that is between about 5 microns and about 20 microns thick. In some variations, a coating may comprise a hydrogel in order to allow for ionic conduction.

Stimulator Chip

Figure 4:
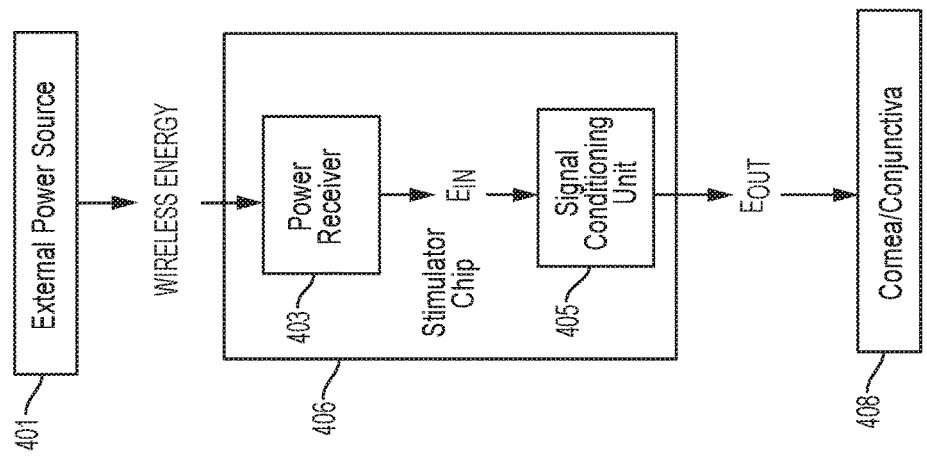
FIG. 4 shows a block diagram illustrating a method of increasing tear production using a stimulator chip.

FIG. 4 shows a block diagram illustrating how tear production may be increased using a stimulator chip as described herein. Generally, an external power 401 source may transmit wireless energy to a stimulator chip 406. The stimulator chip 406 may then convert the energy to a stimulation signal $E_{out}$ comprising an electric waveform, which may be delivered to a subject for electrically stimulating the cornea/conjunctiva 408.

More specifically, the stimulator chip 406 may comprise a power receiver 403 and a signal conditioning unit 405. The power receiver 403 may be supplied with wireless energy from the external power source 401, and may convert the wireless energy to an electric signal $E_{in}$. The signal conditioning unit 405 may receive the electric signal $E_{in}$ and then modify the electric signal $E_{in}$ into the desired electric output $E_{out}$. The signal conditioning unit 405 may modify one or more of the signal's frequency, shape, and amplitude in any suitable manner (e.g., using resistive and capacitive elements, amplifiers). The electric output $E_{out}$ may be a desired stimulation signal and may be delivered via electrode contacts to the cornea/conjunctiva 408 to activate lacrimation. While the variation of the system described with respect to FIG. 4 comprises a signal conditioning unit to modify the signal to the desired electrical stimulus, it should appreciated that in some variations, the signal may additionally or alternatively be manipulated using the external power source (e.g., by pulsing the power source in a particular pattern). With photovoltaics, for the example, manipulation of the signal may be done entirely externally by manipulation of the external power source.

Figure 5:
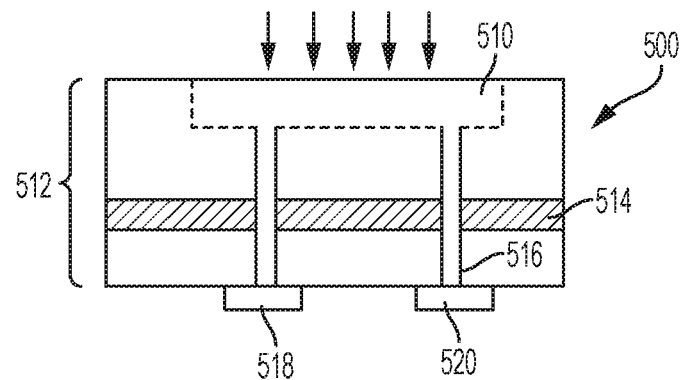
FIG. 5 shows an illustrative variation of a stimulator chip.

In some variations, the stimulator chip may comprise one or more photodiodes, which act as both the power receiver and the signal conditioning unit. FIG. 5 shows a variation of a stimulator chip comprising an integrated circuit 500. The integrated circuit may be formed by semiconductor fabrication techniques on any suitable substrate, such as but not limited to a silicon on insulator (SOI) substrate. FIG. 5 shows an SOI semiconductor substrate 512 having an insulator layer 514. Light pulsed at a higher irradiance than ambient light, depicted by multiple arrows, is transmitted to the stimulator chip, which comprises a photodiode in region 510. The stimulation signal (i.e., the electric output) produced may be delivered through vias 516 to electrode contacts 518, 520 for stimulating the ocular tissue. A stimulator chip comprising a single photodiode, as in FIG. 5, may produce a voltage of up to about 0.6 V, but it should be appreciated that if higher voltage is desired, multiple diodes may be formed in series on the substrate. The stimulator chip may also comprise more than two electrodes in some variations.

The electrodes may each have dimensions (e.g., a diameter) measuring between 50 microns and 150 microns, specifically between 75 microns and 125 microns, or more specifically approximately 100 microns. This may result in an area of neural activation of approximately 100 microns. The electrodes may be made from any suitable material, such as but not limited to platinum or iridium oxide films. The stimulator chip may have a length measuring between 0.5 mm and 1.5 mm, specifically between 0.75 mm and 1.25 mm, or more specifically approximately 1.0 mm. The stimulator chip may have a width measuring between 0.5 mm and 1.5 mm, specifically between 0.75 mm and 1.25 mm, or more specifically approximately 1.0 mm. The stimulator chip may have a thickness measuring between 5 microns and 100 microns, specifically between 10 microns and 50 microns, or more specifically approximately 20 microns. In some variations, the stimulator chip measures 1.0 mm×1.0 mm×20 microns. The above-mentioned dimensions are exemplary only, and are not limited to the ranges provided. The stimulation chip and components thereof may be actually be larger, as their size may be limited only by the ability for the stimulator chip to fit within the contact lens and not block vision, while meeting the cosmetic requirements of the patient.

External Power Source

The external power source may be configured to wirelessly transmit energy to the stimulator chip. The external power source may comprise an on/off switch so it can be turned off when not in use by the patient. The external power source may be handheld or mountable for mounting to locations adjacent to where a patient may look for extended periods of time. Mounting locations include, but are not limited to, a computer monitor, car windshield, television, forward face of a smart phone, tablet, etc. In some variations, the mounting location may be on the frame of eyeglasses. A subject wearing a contact lens or having an implant as described herein may activate the stimulator chip by exposing a portion of the stimulator chip (e.g., a photodiode) to the power source. Moving the eye (e.g., looking up) may expose the stimulator chip to the energy transmitted by the power source.

Figure 6:
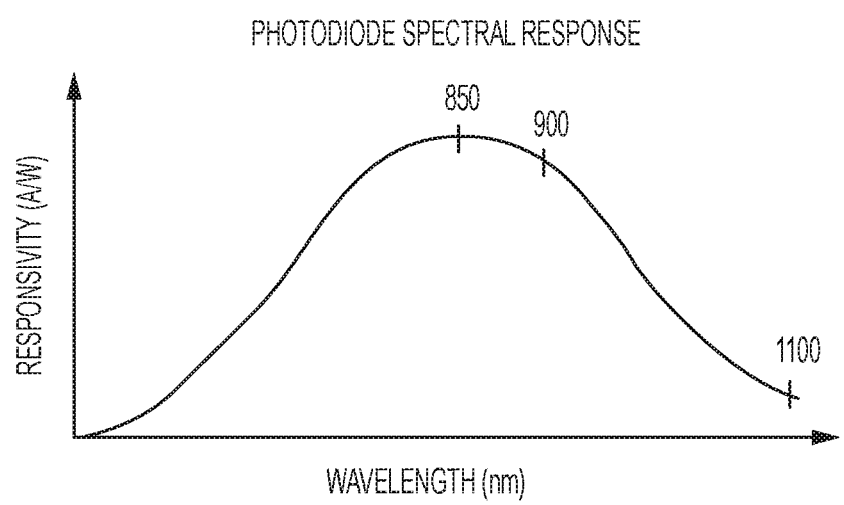
FIG. 6 shows an illustrative variation of the spectral response of a photodiode.

In some variations in which the stimulator chip comprises a photodiode, the power source may comprise a light source, such as a laser diode. A laser diode may produce light within a relatively narrow wavelength band. This wavelength band may be chosen to be specific to the wavelength needed to excite the photodiode, while also avoiding wavelengths visible to humans. The responsivity curve of silicon-based photodiodes may end at approximately 1100 nm, while the human eye may be unable to see high intensity infrared light at wavelengths above approximately 850 nm. Therefore, it may be desirable to select a laser diode producing light comprising wavelengths in the range of approximately 880 nm to approximately 930 nm. FIG. 6 graphically shows the spectral response of an exemplary photodiode that could be used in the current application. In other variations, the external power source may comprise an infrared light-emitting diode (LED).

The desired wavelength range and power of the light transmitted by the power source may provide the energy required to cause the photodiode to generate current, without being phototoxic to the cornea and/or retina. To avoid harming the retina, it may be desirable for the intensity of the source to be below the levels known to cause damage to the retina, as specified in the American National Standard Institute (ANSI) Standards. In some variations, it may be desirable for the intensity of the source to be below the intensity of sunlight. If a photodiode in a stimulator chip as described herein has a surface area of 1 mm$^2$, for example, pulsing the source at a 1% duty cycle may allow for a safe power range up to 100 mW. In some variations, the external power source described herein may emit 10 mW, pulsed at a 1% duty cycle, which is well within a safe range. The power that may be needed to be delivered to the photodiode may vary by device construction. In some variations, for example, the photodiode may require a power of approximately 0.1 mA to approximately 2 mA to generate a desired stimulation signal, and a light intensity of approximately 1 mW/mm$^2$ to approximately 5 mW/mm$^2$ may be needed to generate this. In some variations, the photodiode may require a power of approximately 1 mA to generate a desired stimulation signal, and a light intensity of approximately 3 mW/mm$^2$ may be needed to generate this. However, it should be appreciated that the powers and light intensities desired may vary largely depending on implementation, and the power and intensity desired may increase for chips comprising more than one photodiode (e.g., may in some variations approximately double or triple for variations that utilize two or three diodes, respectively).

Figure 7:
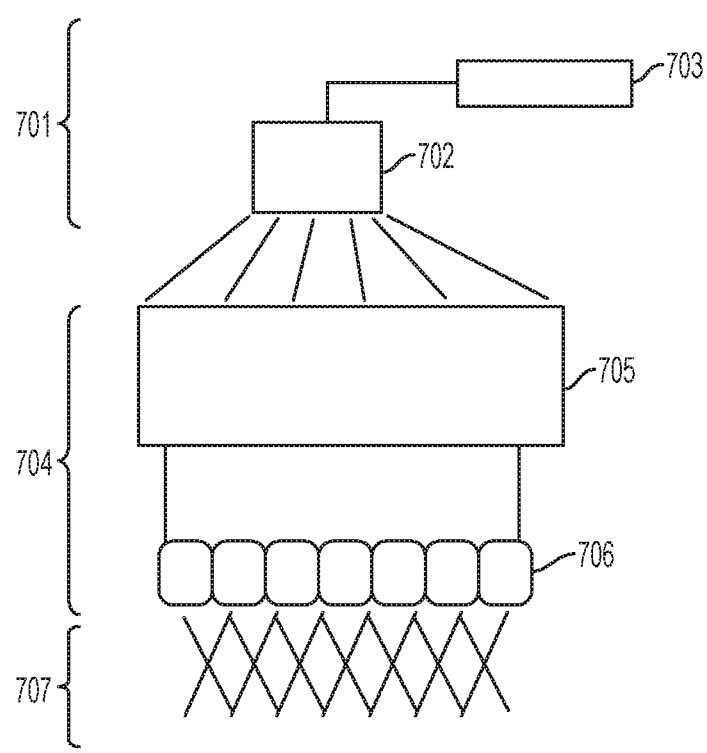
FIG. 7 shows an illustrative variation of an external power source comprising an optical modifier to produce non-collimated light.

It may be desirable for the output of the external light source to be non-collimated. As shown in the diagram of FIG. 7, the external light source 702 may comprise an optical modifier 704 to produce non-collimated light 707. In some variations, the optical modifier 704 may comprise a condenser lens 705 and microlens array 706. The external light source 701 may also in some instances comprise a controller 703, which may modulate the output of the light source 702 to manipulate the desired output stimulus signal, in addition to or instead of a signal conditioning unit of a stimulator chip. In such variations, signal conditioning may be done almost entirely externally, and internal signal conditioning may only limit the voltage and/or current amplitude.

By manipulating the external power source, the electric signals delivered to the subject may be tailored for specific treatment regimens and/or specific subjects. The waveforms may be pulse-based or continuous. When the stimulator is configured to deliver a continuous waveform, the waveform may be a sinusoidal in amplitude and/or pulse-width, or quasi-sinusoidal, square-wave, sawtooth/ramped, or triangular waveform, truncated-versions thereof (e.g., where the waveform plateaus when a certain amplitude is reached), or the like.

In some variations, the stimulator may be configured to vary the frequency and/or pulse width of the waveform. This variation may occur according to a pre-determined plan, or may be configured to occur randomly within given parameters. For example, in some variations the continuous waveform may be configured such that the frequency or pulse width of the waveform varies over time (e.g., according to a sinusoidal function having a beat frequency). In some instances varying the frequency and/or pulse width of a stimulation waveform over time, or pulsing the stimulus on and off (e.g., 1 second on/1 second off, 5 seconds on/5 seconds off), may help reduce subject habituation (in which the subject response to the stimulation decreases during stimulation). Additionally or alternatively, ramping the amplitude of the stimulation waveform at the beginning of stimulation may increase comfort. Patterning may achieve a stronger reflex activation and thereby elicit more tearing in both eyes from stimulation in only one eye.

When the stimulator is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). In some variations, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. In other variations, a biphasic pulse may be asymmetric, where the amplitude and/or pulse width of the first pulse may differ from that of the charge-balancing phase. Additionally, each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa.

In variations where the waveform comprises a biphasic pulse, the biphasic pulse may have any suitable frequency, pulse widths, and amplitudes. For example, in instances where the stimulators described here are used to treat dry eye or otherwise produce a tearing response by stimulating the cornea and/or conjunctiva, the stimulator may be configured to generate a biphasic pulse waveform at a frequency between about 0.1 Hz and about 200 Hz. In some of these variations, the frequency is preferably between about 10 Hz and about 60 Hz. In some of these variations, the frequency is preferably between about 25 Hz and about 35 Hz. In others of these variations, the frequency is preferably between about 50 Hz and about 90 Hz. In some of these variations, the frequency is preferably between about 65 Hz and about 75 Hz. In other variations, the frequency is preferably between about 130 Hz and about 170 Hz. In some of these variations, the frequency is preferably between about 145 Hz and about 155 Hz. In some variations, high frequencies, such as those between about 145 Hz and about 155 Hz may be too high for each pulse to stimulate/activate the target nerves. As a result, the stimulation may be interpreted by the patient to have an element of randomness, which in turn may help to reduce subject habituation.

Similarly, when the stimulus is electrical and the first phase of the biphasic pulse is current-controlled, the first phase may preferably have an amplitude between about 10 µA and 20 mA. In some of these variations, the amplitude may be preferably between about 0.1 mA and about 10 mA. When the first phase of the biphasic pulse is voltage-controlled, the first phase may preferably have an amplitude between about 10 mV and about 25 V. Additionally, the first phase may preferably have a pulse width between about 1 µs and about 10 ms. In some of these variations, the pulse width may preferably be between about 10 µs and about 100 µs. In other variations, the pulse width may preferably be between about 100 µs and about 1 ms.

When an electrical pulse waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 50 Hz), and may have an inter-pulse interval between the first and second pulse of the pair (e.g., about 100 µs, between 50 µs and 150 µs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

As an alternative to optical coupling, power may be transferred to the stimulator chip from the external source using electromagnetic coupling or an electromagnetic telemetry link. For example, in some variations, the contact lens or implant may comprise an inductive coil and rectification circuit. In such variations, the external power source may be manipulated to control the frequency and pulse-width modulation of the stimulation signal.

Systems

Figure 8:
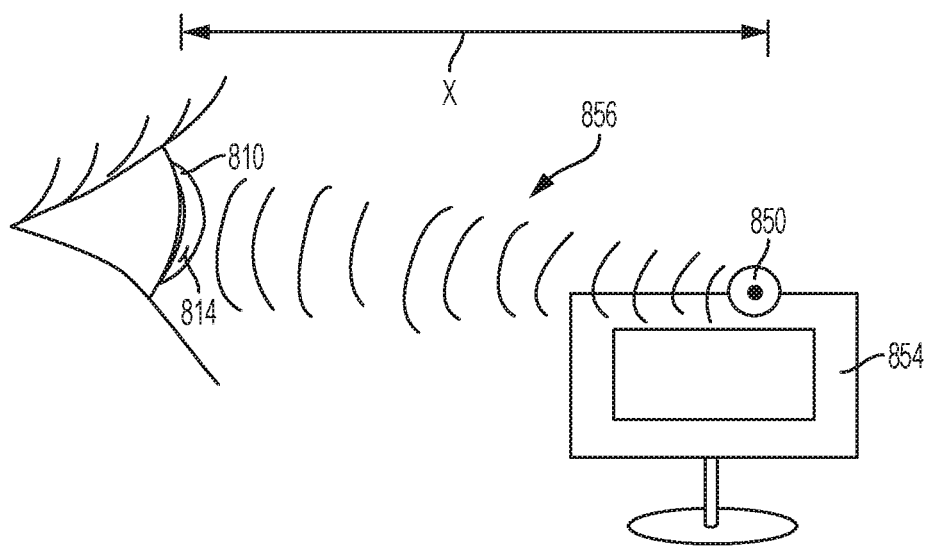
FIG. 8 shows an illustrative variation of a system comprising a contact lens with a stimulator chip and a computer monitor-mounted external power source.

A system as described herein may comprise a device having a stimulator chip and an external power source. The two components may be structurally and functionally configured to work together to increase tear production by stimulating the cornea, conjunctiva, and/or subconjunctiva. The external power source may deliver power and/or signal appropriate to activate the stimulator chip. FIG. 8 shows one variation of a system comprising a contact lens 810 with an embedded stimulator chip 814 as described herein, and a mountable external power source 850 mounted to a computer monitor 854. Transmission of wireless power 856 from the power source 850 to the stimulator chip 814 is illustratively shown. The distance x between the contact lens 810 and the mounted power source 850 is close enough for the stimulator chip 814 to receive the required intensity for the chip to generate the desired electrical stimulus.

Methods

The methods described here may comprise methods for treating dry eye and increasing tear production. Also described are methods for manufacturing a contact lens with an embedded stimulator chip.

Treatment Methods

The methods described here may comprise methods for treating dry eye and increasing tear production in a subject. The methods for increasing tear production may be used to treat a number of eye conditions and can provide immediate relief from discomfort and pain, as well as long-term improvements to overall ocular health. The treatment methods may involve one or more treatment regimens, such as providing stimulation to the cornea, conjunctiva, and/or subconjunctiva on an as-needed basis and/or according to a pre-determined regimen.

The method may be used to treat various forms of dry eye, including (but not limited to), chronic dry eye, episodic dry eye, seasonal dry eye, aqueous deficient dry eye, or evaporative dry eye. In some variations, the methods for increasing tear production may be used for treating DED caused by clinical factors, such as dysfunction of the lacrimal and/or meibomian glands. The treatment may also be for dry eye caused by external factors, such as medications, dehydration, and environmental pollutants. In some instances, the method may be used as a prophylactic measure to treat users who may be at an increased risk of developing dry eye, such as subjects who will undergo or who have undergone ocular surgery such as refractive vision correction and/or cataract surgery. In other instances, the method may be used to treat ocular allergies. For example, an increase in tear production may flush out allergens and other inflammatory mediators from the eyes.

In some variations, the methods for increasing tear production may be for increasing comfort for contact lens wearers. The system may be used in response to discomfort in order to decrease the discomfort associated with contact lens use. The system may also be used in response to discomfort to extend the time period for which an individual can comfortably wear contact lenses. Dryness and other conditions resulting from prolonged use of contact lenses may shorten the lifetime of contact lens use, which is often not past the age of forty. In some variations, the methods for increasing tear production may be for extending the number of years a contact lens user can wear contacts.

In some variations, the methods for increasing tear production may be for reducing the symptoms of tired eye in patients not diagnosed as having DED. Increased tear production may lead to more frequent blinking, which may in turn keep the eyes lubricated and reduce feelings of heaviness and strain.

Generally, the methods may comprise placing a device with a stimulator chip on the cornea or in the subconjunctiva of the eye of a subject. Because the nerves innervating the superior, inferior, and lateral portions of the conjunctiva (the supraorbital nerve, supratrochlear nerve, infratrochlear nerve, infraorbital nerve, and lacrimal nerve) go to the brain stem, stimulation of these nerves in only one eye may result in a bilateral tearing response. Accordingly, the step of placing a device on the cornea or in the subconjunctiva may involve placing the device in only one eye. For example, a subject may use a stimulating contact lens in one eye, and either no contact lens or a non-stimulating corrective contact lens in the other eye. In some variations, placement of the stimulating contact may be alternated between the eyes. In other variations, a subject may wear stimulating contact lenses in both eyes. Similarly, a stimulator chip may be implanted in only one eye to achieve a bilateral effect.

When the device comprises an implant configured to be implanted in the subconjunctival space, it may be implanted behind the lower eyelid, as described in more detail herein, where it can easily be periodically replaced (e.g., every six months) without any visible scarring. In some variations, an implantable device can be replaced by removing the old device and placing a new device in a position next to the previous position on the orbit (e.g., at the 5 o'clock position instead of the 6 o'clock position). This allows the former incision site to heal and recover. The next replacement of the implant may be put in yet another position near the old insertion site but still hidden behind the lower eyelid to avoid cosmetic impact. In some variations, the implantable device can be replaced by removing the old device and placing the new device in the opposite eye. This may reduce accommodation and/or minimize scarring.

In some instances, the eye may be imaged using high-resolution ultrasound, optical coherence tomography (OCT), or other imaging technique prior to implantation. The images may be used, for example, to assist in implanting the device (e.g., how deep to insert the implant based on the thickness of the conjunctiva or to verify that a patient is suitable for the procedure by possessing a conjunctiva that is thick enough to hold such an implanted device with a significant enough safety margin), selecting an appropriately sized/shaped implant for the patient's eye anatomy, and/or determining the source power needed to activate the stimulating chip.

After one or more contacts or implants is located on or in the eye, the methods may further comprise activating the stimulator chip using an external power source, and stimulating the cornea and/or conjunctiva to activate the reflex pathway and increase lacrimation and/or tear quality by increasing meibomian secretion or accessory gland secretion. In variations where the external power source is handheld, the handheld power source may be moved toward the eye, to a distance at which the external power source can deliver the intensity to generate the desired electrical stimulus. The distance can range from approximately 1 cm to approximately 1 m. Power sources at greater distances from the eye may require greater total power to activate the stimulator, due to light spread. In order to limit the total power output, and thus the potential for harming the iris, it may be desirable to have the distance be approximately 5-10 cm. In variations where the external power source is a mountable, the power source may have been mounted to a location adjacent to where the subject may look for extended periods of time, and the eye may be moved toward the external power source. When the external power source comprises an on/off switch, the power source may be turned on. If the stimulator chip is covered by an eyelid when the subject is looking forward, the eyeball (or, additionally or alternatively, the eyelid) may be moved to expose the stimulator chip to the power source.

Activation of the stimulator chip to generate a stimulus, which may in turn cause tearing or other effects, may be performed throughout the day on an as-needed basis and/or according to a pre-determined regimen. In some instances, a user may use one of the devices described herein to provide a round of stimulation when the user experiences symptoms of dry eye. A round of stimulation may have any suitable duration (e.g., between 1 second and 10 minutes). In other instances, the devices may be used to provide stimulation on a scheduled basis. For example, in some variations the devices described here may be used to provide a round of stimulation at least once daily, at least once weekly, or the like. In some variations, the devices may be used to deliver multiple rounds of stimulation each day (e.g., at least two treatments daily, at least four treatments daily, at least six times daily, between four and eight times daily, etc.) In some variations, the stimulation may be delivered at certain times of day. In other variations, the stimulation may be delivered at any time during the day as desired or determined by the user. When the device is used to provide stimulation on a scheduled basis, in some variations each round of stimulation may be the same length (e.g., about 30 seconds, about 1 minute, about 2 minutes, about 3 minutes, about 4 minutes). In other variations, some rounds of stimulation may have different predetermined lengths. In yet other variations, the user may choose the length of the round of stimulation.

Methods of Manufacturing

In some variations, the methods described here comprise methods of manufacturing a contact lens that is configured to increase tear production by stimulating the cornea and/or conjunctiva. The manufacturing method is designed to reproducibly form a lens body with an embedded stimulator chip, where the stimulator chip is in a specific orientation and position within the lens body. Close proximity of the stimulator chip to the eye surface allows for effective stimulation of the cornea, conjunctiva, and/or subconjunctiva, while exposure of the stimulator chip to the eye may result in a foreign body sensation and irritation. Accordingly, in some variations, the stimulator chip may be within 5 microns, within 10 microns, or within 10-20 microns of the posterior surface of the lens.

Lathe Cutting

The methods of manufacturing a contact lens as described herein may comprise the step of embedding a stimulator chip in a lens body by sheet casting or rod casting. The method may further comprise the step of lathe cutting the casting to a desired shape.

When manufacturing the contact lens described here uses sheet casting, as shown in FIG. 9A, stimulator chips 918 may be set into a fixture 950. The stimulator chips 918 may be oriented with the electrodes 928, 930 positioned downwardly in the fixture 950 to create an electrode layer 952, as shown in FIG. 9B. A mix/pre-mix biomaterial may be poured into a mold 954 defined by the fixture 950. The biomaterial may be cured, post-cured, and annealed to create a biomaterial sheet 956, as shown in FIG. 9B. The electrode layer 952 may be sealed by reversing the biomaterial sheet 956, adding a thin film 958, and curing, as shown in FIG. 9C. Overall thickness of the sheet cast may be controlled by the curing time and temperature and thin-film thickness. FIG. 9D shows button development by milling, laser cutting, or coring of the sheets.

When manufacturing a contact lens described here uses rod casting, as shown in FIG. 10A, a rod mold 1050 may be developed. Stimulator chips 1018 may be fixated at pre-set levels/positions within the rod mold 1050. A pre-mix/monomer biomaterial may be poured into mold 1050. The biomaterial may be cured, post-cured, and annealed, as shown in FIG. 10B. FIG. 10C shows the steps of de-molding, and cutting or sawing the rod into buttons. A top view and side view of a button created from rod casting is shown in FIG. 10D.

Once the buttons are formed using sheet casting or rod casting methods, the biomaterial with embedded stimulator chips may be lathe cut to a meniscus shape. The anterior and posterior lathe cuts may be achieved by blocking the button on a chuck using vacuum or wax. The radius may be cut to various shapes and dimensions including aspheric surfaces, toric surfaces, multifocal, diffractive, and the like. Typical shapes for contact lenses are meniscus lenses. FIGS. 11A-11C show the shaping of a lens from button form to a meniscus lens using lathe cutting. FIG. 11A shows a side view of a button 1100 with a stimulator chip 1118. FIG. 11B shows the button of FIG. 11A with an anterior cut defining an anterior surface with three different radii of curvature $R_1$, $R_2$, and $R_3$. FIG. 11C further shows a posterior cut defining an anterior surface with three different radii of curvature $R_4$, $R_5$, and $R_6$.

Control over spacing of the stimulator chip and the posterior surface of the lens may be achieved by appropriately locating the stimulator chip on the button surface during casting stages. Thickness may be controlled using a combination of casting and lathing processes to ensure that the stimulator chip is close to the posterior surface of the contact lens without being exposed, as described in more detail herein.

Cast Molding

Figure 12A:
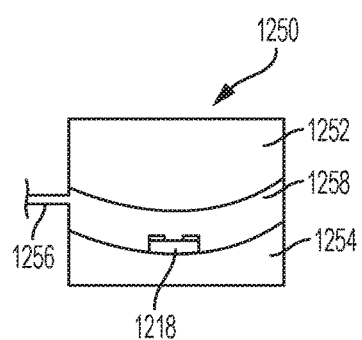
FIGS. 12A-12D show an illustrative variation of a method of manufacturing a contact lens using cast molding.
Figure 12B:
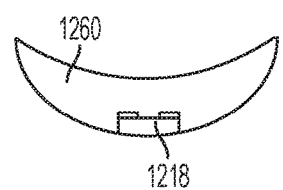

In some variations, the methods of manufacturing a contact lens may comprise embedding a stimulator chip in a lens body and shaping the lens body by direct cast molding. Disposable or metal molds that follow the contour/shape of the lens shown in FIG. 11C may be directly molded using highly polished surfaces (e.g., chrome- or steel-coated metal). As shown in FIG. 12A, a mold 1250 may comprise a first part 1252, a second part 1254, and a port 1256 for receiving a biomaterial. A stimulator chip 1218 may be positioned within the space 1258 created between first and second parts 1252, 1254 of mold 1250. A biomaterial, which may be a monomer mix, for example, may be fed into the space 1258. The biomaterial may be cured, cast, and de-molded to provide the intermediate lens 1260 shown in FIG. 12B.

Figure 12C:
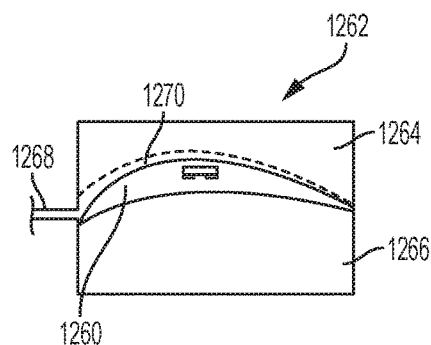
Figure 12D:
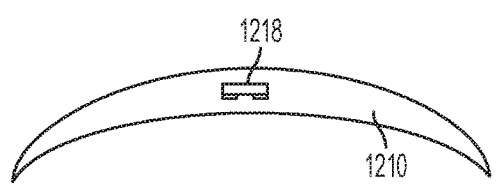

To coat the second surface after cast molding, spray coating or thin-film coating may be employed. In some variations, as shown in FIG. 12C, a second mold 1262 may be used to create a thin layer to form the second surface. Lens 1260 may be placed in a space between a first part 1264 and a second part 1266 of mold 1262. A pre-mix biomaterial may be fed through a port 1268 and into the space, thereby creating a thin layer 1270 to a height of approximately 10-20 microns, or another suitable height as described herein. The biomaterial may be cured and de-molded. FIG. 12D shows a side view of the complete contact lens 1210 comprising the stimulator chip 1218 formed using cast molding method.

The final steps of processing may include hydration, cleaning, packaging, and sterilization or aseptic processing. An additional step of polishing, by tumble or pad for example, may be performed to achieve the surface quality desired.

The invention claimed is:

1. A system for increasing tear production in an eye of a subject, the system comprising:
    a device configured for placement on a cornea, the device comprising:
        a contact lens comprising a lens body;
        a stimulator chip embedded in the lens body and configured to stimulate the cornea or a conjunctiva of the eye, wherein the stimulator chip comprises an integrated circuit; and
        a counterweight embedded in the lens body, wherein the counterweight is non-stimulating and is configured to balance a mass of the stimulator chip, such that the contact lens is rotationally unstable; and
    an external power source for transmitting energy wirelessly to the stimulator chip to activate the stimulator chip.

2. The system of claim 1, wherein the contact lens is a corrective contact lens.

3. The system of claim 1, wherein the contact lens is a non-corrective contact lens.

4. The system of claim 1, wherein the external power source is configured to emit 10 mW, pulsed at a 1% duty cycle.

5. A method of increasing tear production in a subject, comprising:
    transmitting energy wirelessly from an external power source to a stimulator chip, wherein the stimulator chip and a counterweight are embedded in a contact lens worn by the subject, wherein the counterweight is non-stimulating and is configured to balance a mass of the stimulator chip, such that the contact lens is rotationally unstable, and wherein the stimulator chip comprises a photodiode and an electrical contact in communication with the photodiode through a via; and
    delivering a stimulus from the stimulator chip to a conjunctiva or a cornea of the eye to produce tears.

6. The method of claim 5, wherein the external power source comprises a light source.

7. The method of claim 6, wherein the light source comprises a laser diode.

8. The method of claim 6, wherein the light source comprises an infrared light-emitting diode.

9. The method of claim 6, further comprising moving the eye or an eyelid to expose the photodiode to the light source.

10. The method of claim 5, wherein transmitting energy wirelessly from the external power source comprises emitting 10 mW, pulsed at 1% duty cycle, from the external power source.

11. A system for increasing tear production in an eye of a subject, the system comprising:
    a device configured for placement on a cornea, wherein the device comprises:
        a contact lens comprising a lens body;

a stimulator chip embedded in the lens body and configured to stimulate the cornea or a conjunctiva of the eye, wherein the stimulator chip comprises a photodiode and an electrical contact in communication with the photodiode through a via; and a counterweight embedded in the lens body, wherein the counterweight is non-stimulating and is configured to balance a mass of the stimulator chip, such that the contact lens is rotationally unstable; and an external power source for transmitting energy wirelessly to the stimulator chip to activate the stimulator chip.

12. The system of claim 11, wherein the counterweight is located approximately 180 degrees from the stimulator chip.

13. The system of claim 11, wherein the lens body has a posterior surface configured to contact the conjunctiva of the eye, and the stimulator chip is embedded in the lens body within 20 microns of the posterior surface.

14. The system of claim 11, wherein the stimulator chip is embedded in a portion of the lens body that is configured to be in front of an iris of the eye when the device is placed on the cornea of the eye.

15. The system of claim 11, wherein the external power source comprises a laser diode.

16. The system of claim 15, wherein the laser diode produces light comprising wavelengths between approximately 880 nm and 930 nm.

17. The system of claim 11, wherein the external power source comprises an infrared light-emitting diode.

18. The system of claim 11, wherein the external power source comprises an optical modifier to produce non-collimated light.

19. The system of claim 11, wherein the lens body is a corrective lens.

20. The system of claim 11, wherein the lens body has a zero power.

21. The system of claim 11, wherein the external power source is configured to emit 10 mW, pulsed at a 1% duty cycle.

* * * * *